US007495210B2

(12) United States Patent
Li

(10) Patent No.: US 7,495,210 B2
(45) Date of Patent: Feb. 24, 2009

(54) MICRO FLUIDIC GAS ASSISTED IONIZATION DEVICE AND METHOD

(75) Inventor: Gangqiang Li, Palo Alto, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 271 days.

(21) Appl. No.: 11/429,085

(22) Filed: May 4, 2006

(65) Prior Publication Data

US 2008/0067353 A1 Mar. 20, 2008

(51) Int. Cl.
*B01D 59/44* (2006.01)
(52) U.S. Cl. .................. 250/288; 250/281; 250/282
(58) Field of Classification Search .......... 250/281–300
See application file for complete search history.

(56) References Cited

U.S. PATENT DOCUMENTS

| 7,070,682 | B2* | 7/2006 | Lee et al. ............. 204/462 |
| 2003/0026740 | A1 | 2/2003 | Staats |
| 2006/0027744 | A1* | 2/2006 | Stults et al. ............. 250/288 |
| 2006/0060769 | A1* | 3/2006 | Bousse et al. ............. 250/282 |
| 2006/0242832 | A1* | 11/2006 | Weng et al. ............. 29/890.142 |

FOREIGN PATENT DOCUMENTS

| WO | 97/04297 A1 | 2/1997 |
| WO | 00/41214 A1 | 7/2000 |
| WO | 2004/051697 A3 | 6/2004 |
| WO | 2005/019804 A3 | 3/2005 |

OTHER PUBLICATIONS

UK Intellectual Property Office, Patents Act: 1977 Search Report under Section 17, Aug. 15, 2007.

* cited by examiner

*Primary Examiner*—David A. Vanore
*Assistant Examiner*—Andrew Smyth

(57) ABSTRACT

The invention provides a mass spectrometry system, including a microfluidic chip for electrospray ionization having an analyte channel and a gas assist channel that define a spray tip and a detector downstream from the microfluidic chip for detecting ions.

The invention also provides a micro fluidic chip for electrospray ionization including a substrate having an analyte channel, a gas channel and an analyte channel wherein the gas channel and analyte channel exit at the first end to define the electrospray tip.

Methods of using the system and apparatus are also disclosed.

20 Claims, 2 Drawing Sheets

MICRO FLUIDIC GAS ASSISTED IONIZATION DEVICE AND METHOD

BACKGROUND

Atmospheric pressure ionization (API) methods have been widely used to couple chromatographic separations such as high performance liquid chromatograph (LC) or capillary electrophoresis (CE) to mass spectrometers for chemical and biochemical sample analysis. In such systems, the sample effluent from a LC, for instance, is delivered to a capillary placed near the mass spectrometer inlet or interface. By applying a potential difference between the capillary and interface, charge droplets are generated in a continuous spray. Charged droplets further undergo a desolvation process and ion species are generated for mass spectrometry analysis.

Collision between gas molecules and solution facilitate generation of fine droplets. In nanospray techniques it has been common to use direct nebulization without a gas assist. Both pneumatic and direct nebulization methods provide relatively stable spray ionization in case sample effluent contains high concentration of organic solvent. However, for analytes having a higher water content it is often more difficult to form stable spray in a direct nebulization source. Electrospray generated by direct nebulization also contains relatively large droplet which are more likely incompletely desolvated before entering the mass spectrometer. Consequently, high signal to noise is observed. For these reasons, it would be desirable to provide a method or apparatus that more effectively and efficiently ionizes various molecules. These and other problems are addressed by the present invention.

SUMMARY OF THE INVENTION

A mass spectrometry system comprising a microfluidic chip for electrospray ionization comprising a substrate comprising an analyte channel and a gas assist channel that define a spray tip and a detector downstream from the microfluidic chip for detecting ions.

The invention also provides a microfluidic chip for electrospray ionization. The microfluidic chip for electrospray ionization comprises a substrate having a first end with a spray tip, an analyte channel and a first gas channel disposed in the substrate, wherein the analyte channel and gas channel exit at the first end to define the spray tip used for electrospray ionization.

A method for electrospray, comprising ejecting and ionizing a sample from an electrospray tip; and assisting the ionization of the ejected sample by applying a gas stream to the ejected sample.

BRIEF DESCRIPTION OF THE FIGURES

The invention is described in detail below with reference to the following figures.

DETAILED DESCRIPTION OF THE INVENTION

Before describing the invention in detail, it must be noted that, as used in this specification and the appended claims, the singular forms "a," "an," and "the" include plural referents unless the context clearly dictates otherwise. Thus, for example, reference to "a microfluidic chip" includes more than one "microfluidic chip". Reference to a "central layer" includes more than one "central layer". In describing and claiming the present invention, the following terminology will be used in accordance with the definitions set out below.

The term "adjacent" means, near, next to or adjoining. Something adjacent may also be in contact with another component, intersect the other component, surround the other component, be spaced from the other component or contain a portion of the other component. For instance, a central channel that is adjacent to an analyte channel may be spaced next to the channel may contact the channel, or may surround or be surrounded by the channel, may contain, may adjoin the channel or may be near the channel.

The term "detector" refers to any device, apparatus, machine, component, or system that can detect an ion. Detectors may or may not include hardware and software. In a mass spectrometer the common detector includes and/or is coupled to a mass analyzer.

The term "mass spectrometry system" refers to a system comprising at least a micro fluidic chip, an optional ion transport system, a mass analyzer and a detector.

The term "mass analyzer" refers to any number of mass analyzers known in the art for identifying, separating and characterizing molecules.

The term "separation system" refers to any analytical or preparative apparatus that may be used or employed to separated purify or concentrate molecules that will be introduced into the micro fluidic chip.

The term "transport system" refers to any number of conduits, electrodes or other methods known and used in the art for moving molecules from one place to another.

The invention is described with reference to the figures. The figures are not to scale, and in particular, certain dimensions may be exaggerated for clarity of presentation.

Figure 1:
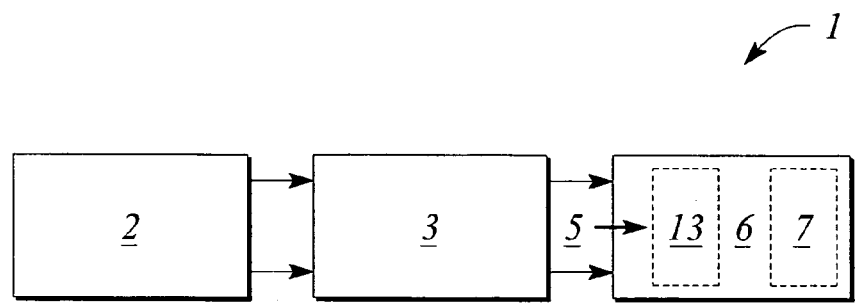
FIG. 1 shows a general block diagram of the system of the present invention.

FIG. 1 shows a general block diagram of the analytcal system 1 of the present invention. The analytical system 1 may comprise an optional separation system 2, a microfluidic chip 3, an optional transport system 5 and a mass spectrometry system 6. The mass spectrometry system 6 comprises a mass analyzer 13 and a detector 7. The block diagram is not to scale and is drawn in a general format because the present invention may be used with a variety of different types of designs and systems. In addition, each of the designs or arrangements may be changed or adjusted. The invention should not be interpreted to be limited to the illustrated embodiments. Each of the systems and/or components will be described in more detail below.

The optional separation system 2 may comprise any number of systems known in the art for separating molecules. More commonly this system may comprise an analytical system such as a liquid chromatography system (LC). However, other systems and methods known in the art may be employed. For instance, the separation system 2 may also comprise an electrophoresis system and/or apparatus, an isoelectric focusing system and/or apparatus, a biorad or similar type preparative electrophoresis system and/or apparatus, an analytical or preparative column, a two dimensional gel, and other systems and/or apparatus that are known in the art for separating molecules. FIG. 1 shows an embodiment of the invention where an analytical system is employed. The analytical system may comprise a high performance liquid chromatography (HPLC) and associated equipment. These parts and designs are well known in the art and are, therefore, not described here in any further detail.

FIGS. 2-5 show more detailed views of the microfluidic chip 3 of the present invention. The microfluidic chip 3 may comprise a single substrate or one or more layers of material (single substrate not shown in drawings). In the case of the embodiment using layers, the layers may be joined or bonded or designed to be fastened or attached in place. Referring to FIGS. 2-5, the microfluidic chip comprises a first outer layer 11, a central layer 13, and a second outer layer 14. The central layer 13 contacts the first outer layer 11 and the second outer layer 14. One or more optional outer layers (not shown in FIGS) may be employed and contact the second outer layer 14 or the first outer layer 11. Other layers and designs or embodiments are possible. The invention should not be interpreted to be limited to the described embodiments. For instance, it can be imagined that a plurality of differing layers may be employed. In addition, the layers may be in differing orientations, stacking arrrangments or positions. The microfluidic chip 3 has a first end 9 with a spray tip 10. The microfluidic chip 3 and/or central layer 13 comprise an analyte channel 15, a first gas channel 17 and a second gas channel 19.

The first outer layer 11 may comprise any number of materials known or employed in the art. For instance, the first outer layer 11 may comprise a polyimide material or other type polymer that may be constructed in a defined arrangement for bonding or attaching the other layers. Each of the layers may be designed of varying compositions and thicknesses. Layers may comprise composite materials, polymers, plastics, metals, stainless steel, semiconductor materials, or any other material known in the art. Other materials not known in the art may also be employed that are capable of being etched or designed with a channel in or through the material.

The central layer 13 may comprise any number of materials known or employed in the art. For instance, the central layer 13 may comprise a polyimide material or other type polymer that may be constructed in a defined arrangement for bonding or attaching the other layers. Central layer 13 may be designed or constructed to attach or be joined to first outer layer 11. Fasteners and adhesives known in the art may be employed to join the central layer 13 and the first outer layer 11. Each of the layers may be designed of varying compositions and thicknesses. Layers may comprise composite materials, polymers, plastics, metals, stainless steel, semiconductor materials, or any other material known in the art. Other materials not known in the art may also be employed that are capable of being etched or designed with a channel in or through the material.

The second outer layer 14 may comprise any number of materials known or employed in the art. For instance, the second outer layer 14 may comprise a polyimide material or other type polymer that may be constructed in a defined arrangement for bonding or attaching the other layers. The second outer layer 14 and/or the central layer 13 may be designed to attach together or be joined. Adhesives know in the art may also be employed for joining second outer layer 14 to the central layer 13.

Each of the layers may be designed of varying compositions and thicknesses. Layers may comprise composite materials, polymers, plastics, metals, stainless steel, semiconductor materials, or any other material known in the art. Other materials not known in the art may also be employed that are capable of being etched or designed with a channel in or through the material.

The transport system 5 is used for transporting ions and moving them from one location to another. The transport system 5 is typically interposed between the microfluidic chip 3 and the mass spectrometry system 6. However, this is not a required configuration.

The transport system 5 may comprise any number of ion transporting devices known in the art. Typically some type of skimmer or ion optics guide may also be employed in the transport system 5. Transport systems 5 are well known in the art and are, therefore, not discussed in detail here.

The mass spectrometry system 6 comprises the mass analyzer 13 and the detector 7. The mass analyzer 13 is used for separating and determining the m/Z ratio of the ions produced by an ion source. In certain instances the mass spectrometry system 6 may also comprise the microfluidic chip 3.

The detector 7 is positioned downstream from the transport system 5 and may comprise any number of detectors known and used in the art. Some typical detectors may include photomultiplier tubes or other similar type technology. The detectors may be coupled to a computer and interface for output of the results to a third party user interface (not shown in the FIGS.).

Figure 2:
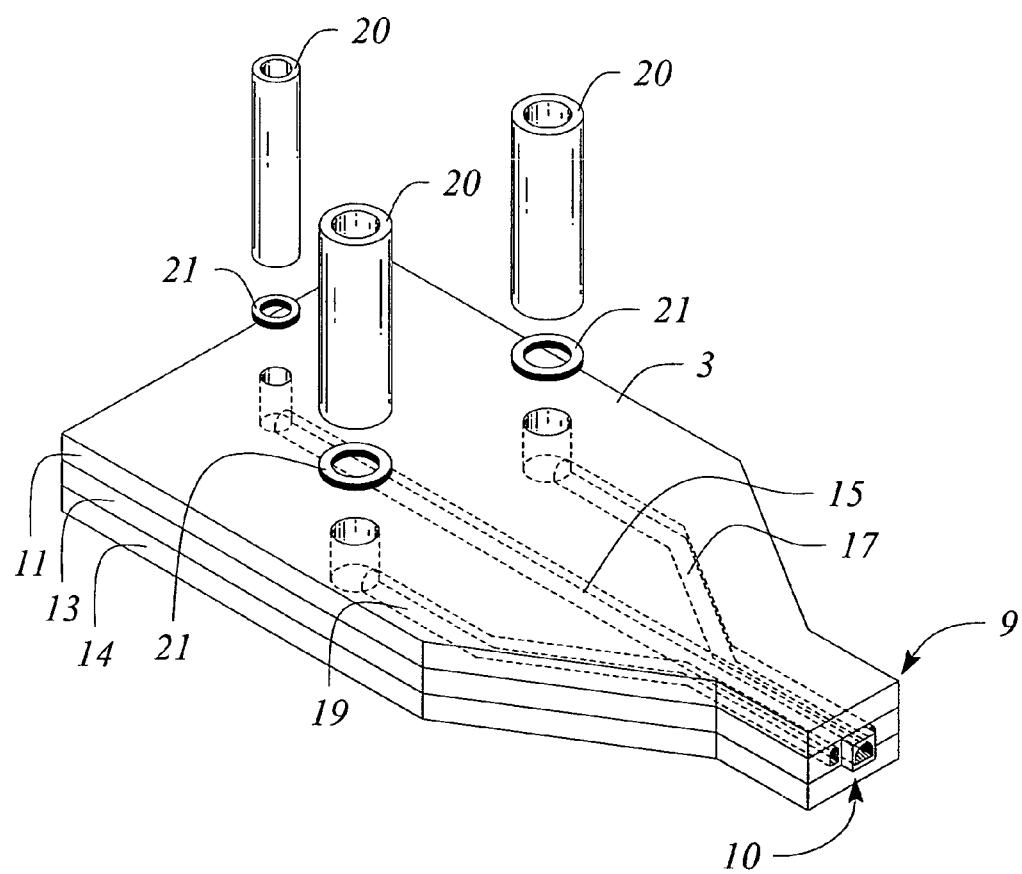
FIG. 2 shows a perspective view of the present invention.
Figure 3:
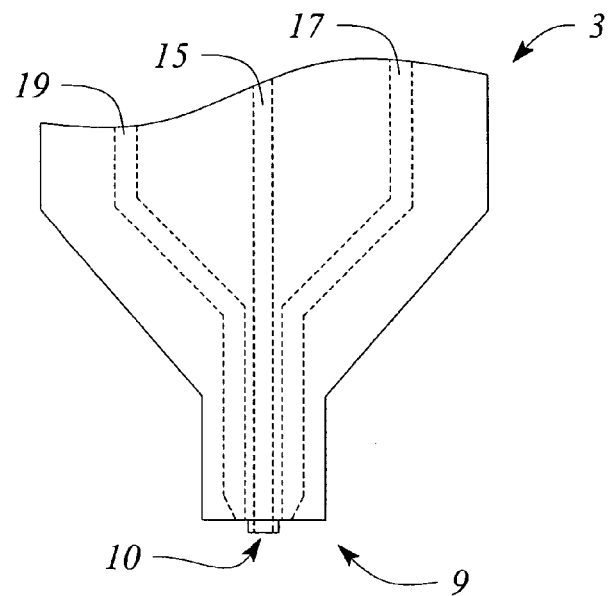
FIG. 3 shows a plan view of the present invention.

FIG. 2 shows a perspective view of the microfluidic chip 3 of the present invention. The figure shows additional details of the analyte channel 15, the first gas channel 17 and the second gas channel 19. A series of one or more connection conduits 20 and/or sealing gaskets 21 may be employed with the present invention for coupling the microfluidic chip 3 to one or more analyte and/or gas sources. It should be noted that other channels may be employed with the present invention. In no case should the present embodiments be interpreted to limit the scope of the invention. For instance, various number and channels with differing orientations, designs, volumes and valves may also be employed with the present invention. It can be imagined that a series of valves may also be employed to help in chemical reactions and mixing. Various valves can be designed to open and close in varying channels to promote mixing of molecules at various stoichiometric amounts. Each of the channels may also be designed for carrying various volumes, flow rates and pressures. These parameters can be further designed and improved based on the samples that are employed. The channels may be designed and/or constructed by using various techniques known in the art. For instance, the channels may be designed using laser ablation techniques, etching, or other similar type methods know in the art. Other gas channels and embodiments may be employed. It is important to the invention that each of the channels exit at a common end. In the diagram the first gas channel 17, the analyte channel 15 and the second gas channel 19 all exit at the first end 9. They end at the first end 9 to define the spray tip 10. The diagram shows each of the channels being oriented parallel to each other. This is not a requirement of the invention. In other embodiments or designs the channels may be, non-parallel, perpendicular, non-linear, linear or in any various arrangement in which they intersect. Various mixing or other channel or chambers may be employed with the present invention.

Figure 4:
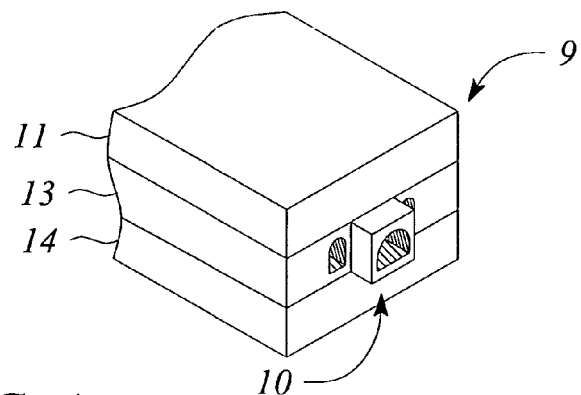
FIG. 4 shows a perspective view of the present invention.
Figure 5:
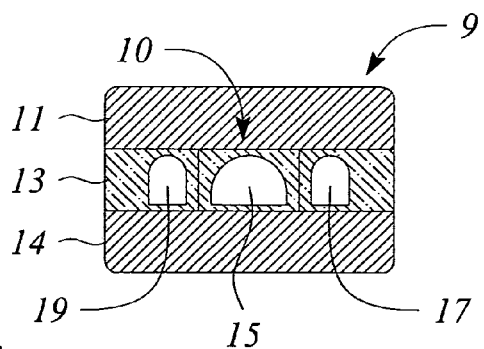
FIG. 5 shows a cross-sectional view of the present invention.

FIGS. 4 and 5 show cross-sectional views of the microfluidic chip 3 of the present invention. The figures show the first gas channel 17, the second gas channel 19 and the analyte channel 15. The first gas channel 17, the second gas channel 19 and the analyte channel 15 are disposed in the central layer 13 or a portion of the central layer 13. This is not a requirement of the invention. In certain embodiments it can be imagined that other analyte and/or gas channels may be employed. In certain embodiments the analyte channel 15 may be designed for conducting separations of the sample or analyte molecules. Various techniques are known in the art for building microfluidic chips for actual separations in situ. This type of design eliminates the need for optional separation system 2. However, in certain cases the separation system 2 may also be employed in conjunction with an analyte channel 15. This would be in the case that the separation system 2 performs separations of certain molecules and then the analyte channel performs a follow up separation or further purification. In addition, the first gas channel 17 and/or the second gas channel 19 may be disposed in the outer layer 11 and/or second outer layer 14 or a portion of one or more of these layers. The analyte channel 15 may be disposed in the central layer 13 as shown and/or in one or more of the outer layers 11 and/or 14. The analyte channel 15 may also be disposed in a portion of one or more of these layers. The first gas channel 17, the second gas channel 19 and the anaylte channel 15 may be designed in both symmetric and non-symmetric orientations relative to each other. The present figures show each of the channels aligned with each other in a symmetric or parallel orientation as they extend down the microfluidic chip 3. This is not a requirement of the invention. It can be imagined that each of these channels may be designed to intersect or be disposed in a non linear or non-symmetric arrangement to each other.

Having discussed the apparatus of the invention in detail, a description of the method of operation of the invention is now in order. Referring now to FIGS. 1-5, the method of operation begins by the introduction of a sample into the analytical system 1. The sample may be first subject to separation, purification or isolation by separation system 2. After having been purified or separated into distinct components, the sample is directed through a series of channels, conduits or chambers to the microfluidic chip 3, where it is received by the analyte channel 15. The sample travels down the analyte channel 15 until it reaches the first end 9 and spray tip 10. The spray tip 10 may be maintained at atmospheric pressure, below atmospheric pressure or above atmospheric pressure. Pressure for operating electropray apparatus are well known and employed in the art. The sample is then sprayed out of the spray tip 10 and ionized. The first gas channel 17 and the second gas channel 19 are used to assist the nebulization of the sample. It should be noted that certain embodiments may be designed to comprise only one gas channel. In other embodiments it can be imagined that multiple gas channels may be designed. As shown in FIGS. 1-4, the gas channels are constructed near the spray tip 10. Both gas channels may be identical and arranged symmetrically on each side of the spray tip 10. The gas channels may also be formed using laser ablation on the central layer 13. The end of the first gas channel 17 and the second gas channel 19 are typically placed 20 to 500 micrometers behind the end of the analyte channel 15. The first gas channel 17 and the second gas channel 19 may have a similar size or dimension to the analyte channel 15. Dimensions may range from about 10 to 200 micrometers. However, the cross-sectional area of the end of the gas channel may be considerably smaller (i.e. around 10 micrometers). Due to its smaller dimension, a pressure drop occurs at the end of the gas channels so that high speed gas stream is produced. For instance, pressure may be applied to the gas at a pressure from 5 to 100 PSI to the gas channels, gas jets are formed at the ends of the gas channels. Various gases may be employed with the present invention. For instance, air, argon, nitrogen, etc. may be employed with the present invention. The invention may utilize any number of different gases or combination of gases that are know or used in the art. The gas jets facilitate the spray ionization. Depending on composition of analyte and other ionization conditions, gas pressure can be varied or completely turned off. Generally, applying gas assisted spray ionization produced more stable sprays, especially when the solution is aqueous.

Optimally, the end of the gas channel is tapered toward the analyte channel 15 as shown in the FIG. 2, so the gas stream cuts across the analyte at the spray tip 10. Voltages can be applied to either the microfluidic chip 3 or interface. In other words, the microfluidic chip 3 or the interface may be maintained at ground. Electrospray ionization is formed when a voltage of 1500 to 2500 volts is applied between the spray tip 10 and the mass spectrometer interface (not shown). These techniques, designs and methods are well known in the art. The polarity can be adjusted based on the ion of interest. The ions that are produced by the microfluidic chip 3 may then be detected by the detector 7. The spray tip 10 may be maintained under vacuum, at atmospheric pressure or below atmospheric pressure to improve overall detection results and signal to noise ratios. In other embodiments, the gas introduced into the analyte and/or analyte channel 15 may be employed to perform mixing, solution chemistry or solution chemical reactions.

I claim:

1. A microfluidic chip for electro spray ionization, comprising:
   (a) a first end comprising a spray tip;
   (b) a first outer layer;
   (c) a central layer contacting the first outer layer, the central layer defining features comprising an analyte channel, a first gas channel and a second gas channel; and
   (d) a second outer layer contacting the central layer;
   wherein the analyte channel, the first gas channel and the second gas channel separately exit at the first end to define the spray tip for electrospray ionization.

2. A microfluidic chip as recited in claim 1, wherein the analyte channel is disposed in a portion of the first outer layer.

3. A microfluidic chip as recited in claim 1, wherein the analyte channel is disposed in a portion of the central layer.

4. A microfluidic chip as recited in claim 1, wherein the analyte channel is disposed in a portion of the second outer layer.

5. A microfluidic chip as recited in claim 1, further comprising a third outer layer contacting the second outer layer.

6. A microfluidic chip as recited in claim 1, wherein the spray tip is at about atmospheric pressure.

7. A microfluidic chip as recited in claim 1, wherein the spray tip is below atmospheric pressure.

8. A microfluidic chip as recited in claim 1, wherein the spray tip is above atmospheric pressure.

9. A microfluidic chip for electrospray ionization, comprising:
   (a) a substrate comprising a first end with a spray tip, an analyte channel and a gas channel, wherein the analyte channel and gas channel separately exit at the first end to define the spray tip used for electrospray ionization.

10. A microfluidic chip as recited in claim 9, further comprising a first outer layer.

11. A microfluidic chip as recited in claim 10, further comprising a central layer.

12. A microfluidic chip as recited in claim 11, further comprising a second outer layer.

13. A mass spectrometry system, comprising:
   (a) a microfluidic chip for electrospray ionization comprising an analyte channel and a gas channel that separately exit the microfluidic chip and define a spray tip; and
   (b) a detector downstream from the microfluidic chip for detecting ions.

14. A mass spectrometry system as recited in claim 13, further comprising a separation system.

15. A method for electrospray, comprising:
   (a) ejecting and ionizing a sample from an electrospray tip; and
   (b) assisting the ionization of the ejected sample by separately applying a gas stream to the ejected sample.

16. A method as recited in claim 15, wherein the electrospray tip is in fluid communication with a microfluidic device.

17. A method as recited in claim 15, wherein the electrospray tip comprises a portion of a microfluidic device.

18. A microfluidic chip as recited in claim 1, wherein the first gas channel and the second gas channel taper toward the analyte channel near the spray tip.

19. A mass spectrometry system as recited in claim 13, wherein the gas channel tapers toward the analyte channel near the spray tip.

20. A method as recited in claim 15, further comprising applying the gas stream to the ejected sample so that the gas stream cuts across the ejected sample at the electrospray tip.

* * * * *

UNITED STATES PATENT AND TRADEMARK OFFICE
CERTIFICATE OF CORRECTION

PATENT NO. : 7,495,210 B2
APPLICATION NO. : 11/429085
DATED : February 24, 2009
INVENTOR(S) : Li It is certified that error appears in the above-identified patent and that said Letters Patent is hereby corrected as shown below:

In column 6, line 19, in Claim 1, delete "electro spray" and insert -- electrospray --, therefor.

Signed and Sealed this

Twenty-third Day of June, 2009

JOHN DOLL
*Acting Director of the United States Patent and Trademark Office*